United States Patent [19]

Leise, Jr.

[11] Patent Number: 4,938,750
[45] Date of Patent: Jul. 3, 1990

[54] POUCH WITH SELECTIVE MULTIPLE DEODORIZING FILTERS

[75] Inventor: Walter F. Leise, Jr., Yardley, Pa.

[73] Assignee: E. R. Squibb & Sons, Inc., Princeton, N.J.

[21] Appl. No.: 367,364

[22] Filed: Jun. 16, 1989

[51] Int. Cl.⁵ .............................................. A61F 5/44
[52] U.S. Cl. .................................... 604/333; 55/385.4
[58] Field of Search ............... 604/332, 333, 336, 337; 55/385.4, 159

[56] References Cited

U.S. PATENT DOCUMENTS

| 2,555,086 | 5/1951 | Guinn | 604/333 |
| 4,479,818 | 10/1984 | Briggs et al. | 55/385.4 |
| 4,490,145 | 12/1984 | Campbell | 604/333 |
| 4,723,951 | 2/1988 | Steer | 604/333 |
| 4,732,592 | 3/1988 | Spengler | 55/473 |

FOREIGN PATENT DOCUMENTS 2149306  6/1985  United Kingdom ................ 604/333

Primary Examiner—J. L. Kruter
Attorney, Agent, or Firm—James & Franklin

[57] ABSTRACT

A member in the form of an overfilm or molded housing affixed to the pouch wall has a plurality of isolated vent passages. A separate filter assembly is situated in each of the passages. Adhesive coated covers are situated to obstruct the flow through all but a selected one of the passages. After the filter in the unobstructed passage has lost its effectiveness, the cover is removed from another passage and placed over the passage containing the used filter to obstruct same. The filter in each passage is used, in turn, by appropriate movement of the cover, until all of the filters have been used.

12 Claims, 4 Drawing Sheets

POUCH WITH SELECTIVE MULTIPLE DEODORIZING FILTERS

BACKGROUND OF THE INVENTION

The present invention relates to a medical device including a collection pouch such as an ostomy, wound care or similar pouch and, more particularly, to a pouch with multiple odor absorbing vent filters.

Certain types of abdominal surgery, such as colostomies, ileostomies and urostomies result in an opening in the abdominal wall, known as a stoma, through which waste is discharged. Since the patient has no control over the waste discharge, a device including a waste collection receptacle or pouch is utilized in order to protect the stoma and collect the waste as it is discharged. Similarly, wound irrigation and other medical procedures require the use of devices which include collection receptacles or pouches in various forms.

Many different types of collection receptacles are known. In general, they include a thin walled pouch or bag which is affixed to the body surrounding the wound or stoma. The pouch or bag collects solid, semisolid and gaseous waste. Because the pouch is closed, the accumulation of gas within the pouch may become a problem. It can cause a distension of the pouch which may be distressing and/or embarrassing to the patient. However, the release of the gas may result in an odor which can be unpleasant and embarrassing as well.

In order to overcome the problem of gas buildup within the pouch, it has been suggested that the pouch be provided with a tortuous path vent. It has also been suggested that a deodorizing filter be used within the vent.

DESCRIPTION OF THE RELATED ART

One example of an ostomy device with the deodorizing filter is disclosed in Campbell Pat. No. 4,490,145 issued Dec. 25, 1984 and entitled Ostomy Pouch with Deodorizing Filter. That patent features an ostomy pouch having a filter element affixed to the outer pouch wall. The outer pouch wall also has an aperture. The filter element includes a polymeric film cover and an insert of gas deodorizing material. The film cover also has an aperture and opposite ends of the insert overlie the two apertures. The Campbell patent also refers to a number of other patents which have dealt with this problem and the reader is referred thereto for additional background information.

Through usage it has been observed that a single deodorizing filter, particularly when used on pouches which are designed to be removed and reused repeatedly, will lose its effectiveness before the end of the useful life of the pouch. Hence, it is the useful life of the filter which limits the useful life of the pouch. Because of this, it has become desirable to find a way to extend the useful life of the filter. Since it has not been practical to accomplish this by employing better filter materials or structures, other courses of action have been considered.

One attempt to overcome problems associated with the limited useful life of filters is disclosed in Steer Pat. No. 4,723,951 issued Feb. 9, 1988 and entitled Gas Filter Arrangement for Ostomy or Ileostomy Bags. That patent features an ostomy bag adapted to receive a replaceable flatus filter which is attached to it by a stack or series of sequentially peelable adhesive annuli. The filter can be changed by peeling off the top annulus (and hence the filter to which it is mounted) in such a way so as to expose an adhesive surface of the annulus next in sequence and sticking a new filter onto the adhesive. In this way, filters can be replaced as needed.

The Steer arrangement requires a patient to peel relatively delicate adhesive annuli, one at a time, from the stack without removing the underlying annuli, a task which may be difficult for the elderly or infirmed because it requires a reasonable amount of dexterity. The present invention offers a solution to the problem of the limited filter life without requiring a complicated series of adhesive members or the careful sequential removal thereof by the patient.

SUMMARY OF THE INVENTION

In general, my solution to the problem is to provide a member on the pouch wall which has a plurality of vent passages, each containing a separate deodorizing filter. Each filter can be exposed in turn by simply moving an adhesive cover from one location to the next. By positioning the covers appropriately, only a single selected deodorizing filter is used at a time, the others being blocked by the covers. In this manner, as many filters as are required (given the space limitations) could be provided on the pouch, such that the useful life of the pouch is no longer limited by the useful life of a single filter. As a practical matter, the anticipated useful life of the pouch is such that only a relatively small number of filters, for example three, are required.

It is, therefore, a prime object of the present invention to provide a pouch with multiple deodorizing filters.

It is another object of the present invention to provide a pouch with multiple deodorizing filters which can be employed in turn.

It is another object of the present invention to provide a pouch with multiple deodorizing filters which are selectable by simply moving a cover from one location to another, a task easily performed by the elderly or infirmed.

It is another object of the present invention to provide a pouch with multiple deodorizing filters wherein adhesive coated covers are utilized to obstruct the passages in which the filters are situated.

It is another object of the present invention to provide a pouch with multiple deodorizing filters which can be manufactured using conventional manufacturing techniques and which is adapted to utilize commercially available filter elements to reduce the cost thereof.

In accordance with the one object of the present invention, a medical device is provided including a waste receptacle in the form of a thin walled pouch. A member is affixed to the pouch wall which comprises a plurality of isolated passages. Each of the passages constitutes a vent. Deodorizing filter means are situated in each of the passages. Means are also provided which are associable with each of the passages for obstructing the flow through all but a selected one of the passages.

The passages in the member each include a filter means receiving recess. Gas impervious barriers are interposed between the recesses.

The obstructing means preferably comprises cover means. Means are provided for affixing the cover means to the member in alignment with the passages. Preferably, the cover means is adhesively affixably to the member.

The member is preferably in the form of a stamped overfilm or is a molded plastic housing. It is affixed to the pouch wall over a vent opening.

The filter means preferably include activated charcoal filter assemblies. More specifically, the filter means may include a polyurethane foam impregnated body with carbon granules.

Each of the passages has an inlet and an outlet. The filter means is interposed between the inlet and the outlet. The inlet and the outlet of each passage are preferably aligned such that flow through the filter means is in a direction substantially perpendicular to its surface, from the inlet to the outlet. The filter means is preferably substantially liquid impervious.

In accordance with another aspect of the present invention, a medical device is provided including a waste receptacle in the form of a thin walled pouch. A member is affixed to the pouch and includes a plurality of isolated passages, each having an inlet and an outlet so as to constitute a gas vent. Substantially liquid impervious deodorizing filter means are interposed between the inlet and the outlet in each passage. Removable cover means are affixable to the member for obstructing the outlets associated with all but a selected one of the passages.

To these and such other objects which may hereinafter appear, the present invention relates to a pouch with multiple deodorizing filters as described in the following specification and recited in the annexed claims, taken together with the accompanying drawings, wherein like numerals refer to like parts and in which:

DESCRIPTION OF THE PREFERRED EMBODIMENT

While the drawings illustrate the present invention in conjunction with an ostomy pouch, it should be appreciated that the present invention may find application with respect to a variety of different medical devices which include thin walled collection receptacles in the form of a pouch or a bag. The particular intended use of the pouch should not be considered a limitation on the present invention and it is believed that one skilled in the art could adapt the present invention for utilization on a variety of different collection receptacles without substantial difficulty.

The drawings illustrate the top section of a thin walled ostomy pouch, generally designated 10, having an exterior wall 12 and an interior wall 14 heat welded along their periphery to form a collection receptacle, as is conventional in the art. The particular pouch illustrated is of the so-called two piece or detachable variety and may be the type disclosed in U.S. Pat. No. 4,460,363, issued July 17, 1984 to Steer et al., and entitled Ostomy Bag, which discloses an ostomy device currently commercially available for the ConvaTec division of E. R. Squibb & Sons, Inc., of Princeton, New Jersey.

The Steer patent teaches an ostomy pouch which is connected to an adhesive faceplate or dressing, affixed to the patient, through the use of plastic coupling rings which snap together and apart to permit the bag to be removed and remounted without disturbing the dressing. Numeral 16 refers to the relatively rigid plastic coupling ring which is heat welded to the interior wall 14 of the pouch. Ring 16 defines the stoma receiving opening 18 in the pouch. Ring 16 is designed to engage a similar coupling ring on the adhesive dressing (not shown).

Figure 1:
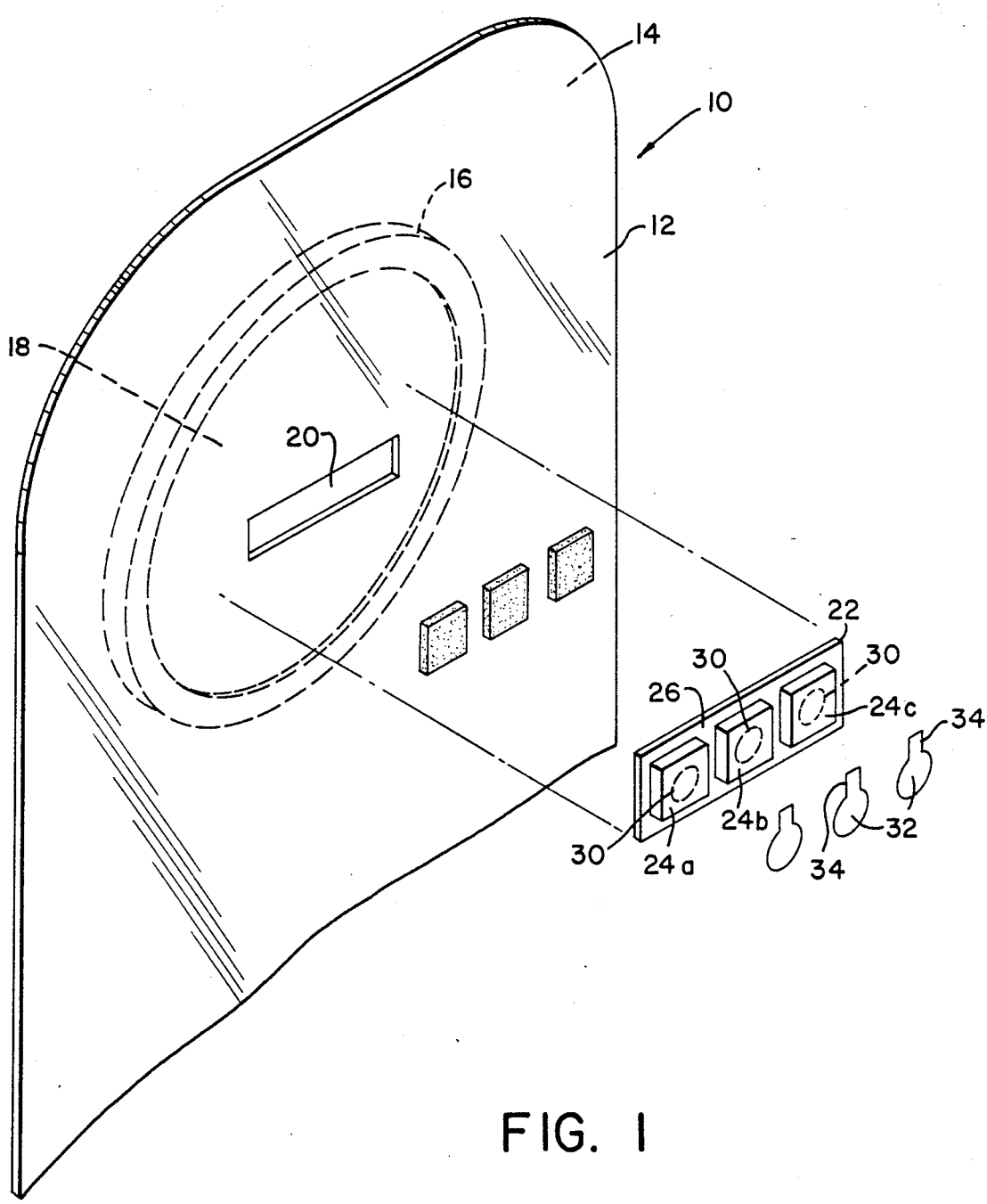
FIG. 1 is an exploded isometric view of an exterior side of the top section of a collection pouch of an ostomy device which incorporates the present invention.
Figure 3:
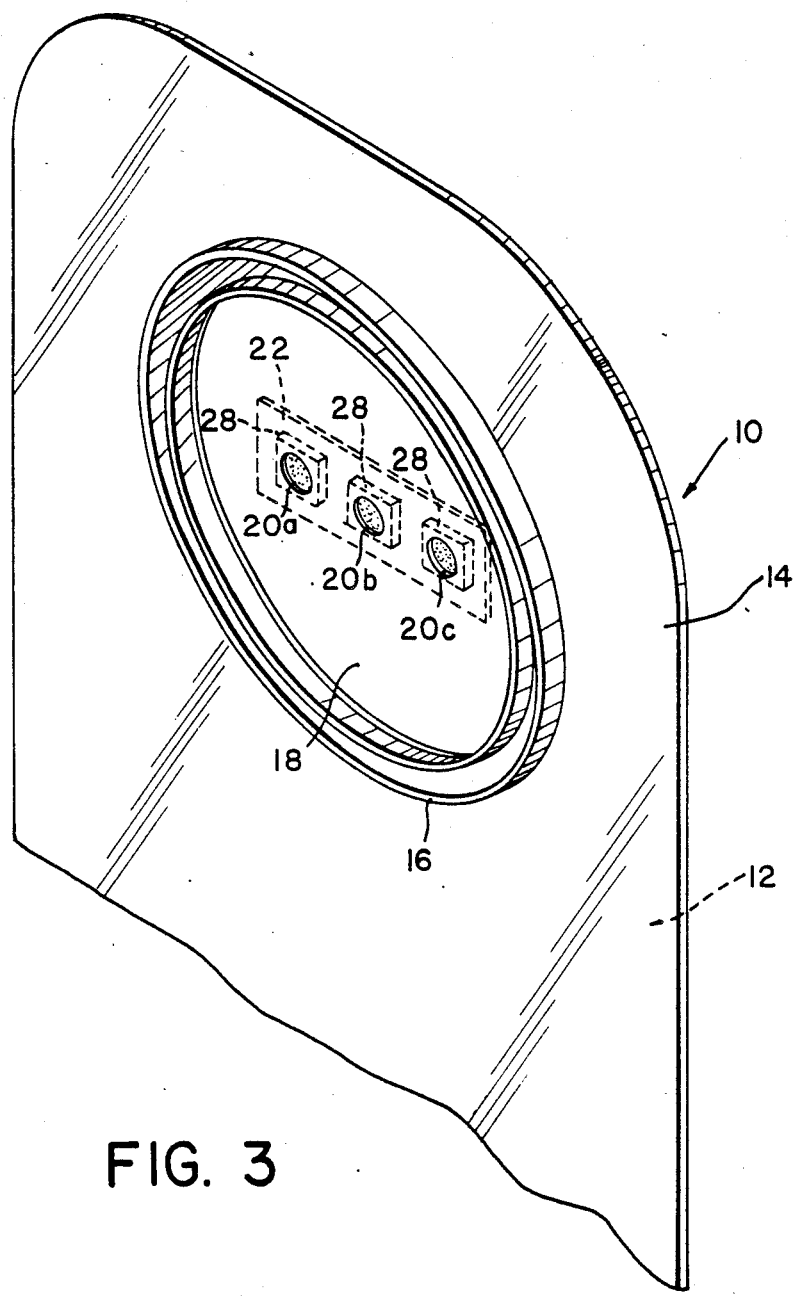
FIG. 3 is an isometric view of the interior side of the top section of a collection pouch similar to that illustrated in FIG. 1 modified to include small individual vent openings instead of a single large vent opening.
Figure 4:
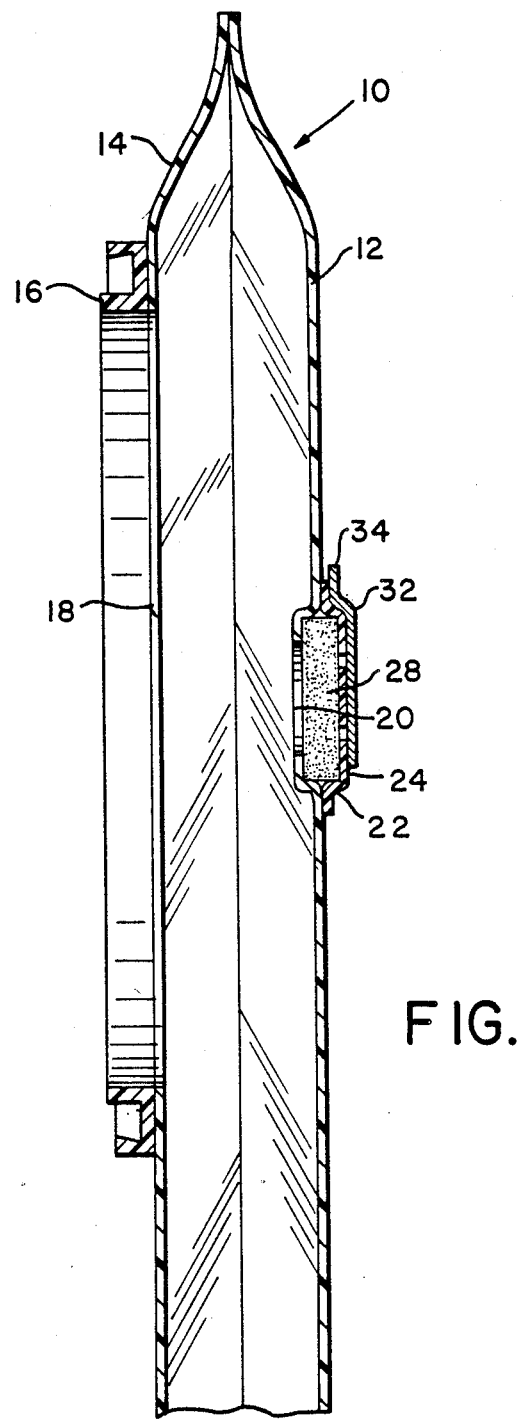
FIG. 4 is a cross-sectional view taken along line 4—4 of FIG. 2.

In exterior wall 12 of pouch 10 is a vent opening 20, preferably aligned with stoma receiving opening 18. In FIG. 1, vent opening 20 is shown as a single, relatively large, generally rectangularly shaped opening through wall 12. In FIG. 3, vent 20 is illustrated as three individual openings 20a, 20b and 20c. Affixed to exterior wall 12, along the border of vent 20, is a member 22 which may consist of a stamped overfilm or a plastic molded housing. Member 22 may be affixed to exterior wall 12 adjacent vent 20 by heat or sonic welding, adhesive or any similar conventional method of forming a fluid tight, mechanically strong seal.

Member 22 is illustrated as including three separate box-like filter receiving chambers or receptacles 24a, 24b and 24c, each of which defines a separate gas vent between the interior of the pouch and the atmosphere. Receptacles 24 protrude from the surface 26 of member 22 such that gas impermeable barriers are formed therebetween. Hence, each of the receptacles is isolated from the adjacent receptacles. The receptacles form three parallel but separate vent passages.

Within each of the receptacles 24 is situated a separate filter assembly 28 preferably containing activated carbon as the gas absorbing and deodorizing agent. One type of suitable material is a sheet of foamed, open-cell, synthetic, polymeric material, for example, polyurethane having a large number of activated carbon particles distributed over one of its major surfaces. Such a material is commercially available under the trade name BONDINA. Another type of suitable deodorizing material is a felt pad impregnated with activated carbon in a fine, particulate form. Various types of such carbon cloth are commercially available.

The filter assembly is preferably made by cutting the shape from a sheet of filter medium known as "Bondina" activated carbon filter No. S442. Preferably the filter assembly includes a barrier layer which is liquid impermeable. The barrier layer can be made from a microporous adhesive tape such as that taught by Koplan in U.S. Pat. No. 3,121,021 or from a commercially available "Bondina" non-woven viscus medical tape No. T1562F. The barrier layer can be on one or both sides of the activated carbon sheet, as is desired. Hence, each of the filter assemblies is gas permeable but liquid impermeable. It should be appreciated that while the drawings illustrate the filter assemblies 28 and receptacles 24 as being box-like, this configuration is simply illustrative and other configurations such as round or oval will operate with equal result.

The exterior surface of each of the filter receptacles 24 are provided with a plurality of small openings 30 shown as arranged in a circular configuration. A cover 32 in the form of a substantially circular section of pressure sensitive adhesive tape is designed to be affixed to the exterior surface of the receptacle 24 so as to obstruct vent openings 30. It is required that the number of covers supplied with a pouch be at least as great as one less than the number of passages through member 22. In this way, all but a single selected passage will be obstructed by the covers 32. Covers 32 are preferably provided with an outwardly extending tab 34 to facilitate removal thereof.

Figure 2:
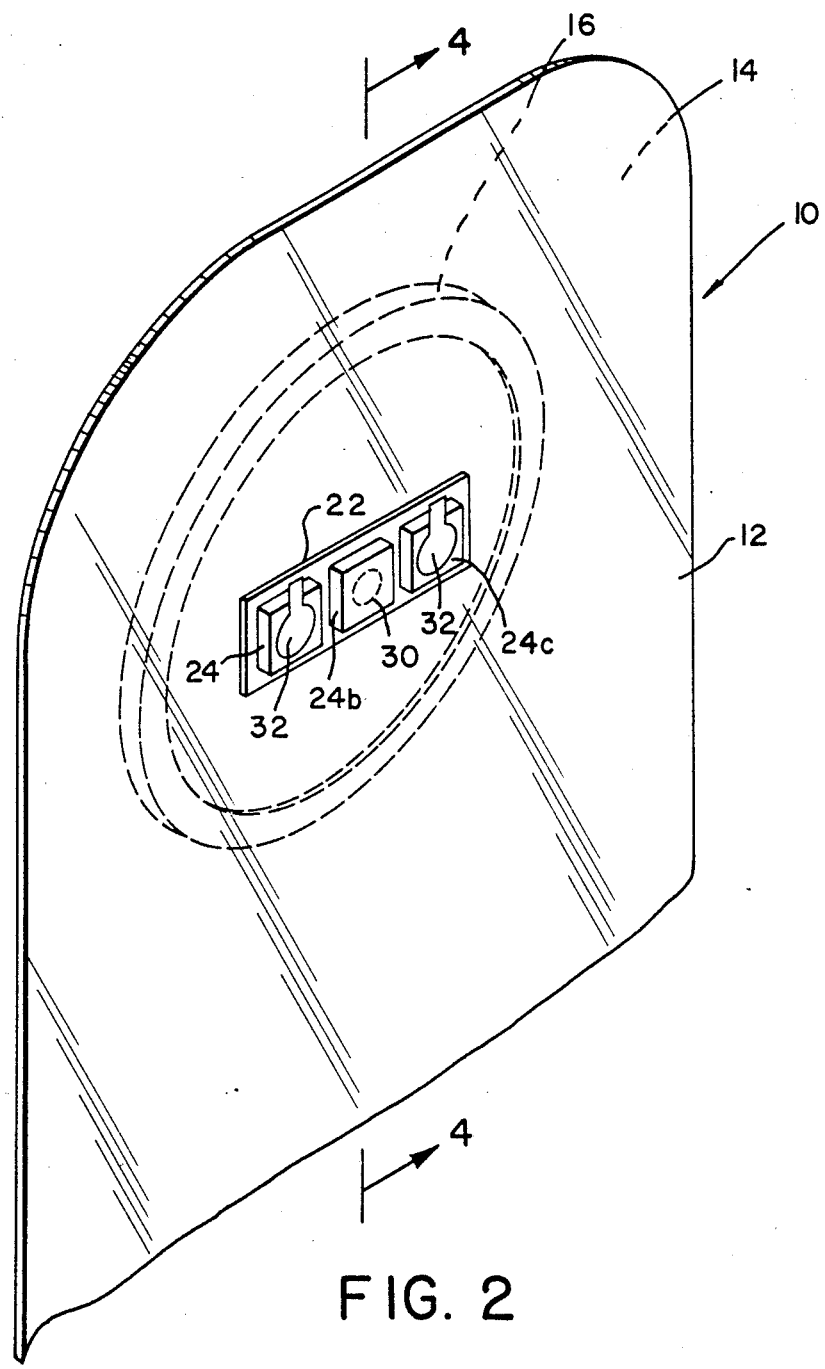
FIG. 2 is an isometric view of a pouch including the present invention showing same as it would appear in use.

In operation, cover 32 is absent over one of the filter assembly receptacles, such as the left most receptacle as shown in FIG. 1. The pouch is used until the filter assembly 28 in the unobstructed passage loses its effectiveness. Thereafter, a different passage is selected, such as the middle passage, and the cover 32 obstructing the middle passage is removed and placed over the previously used passage so as to obstruct same. The device then appears as shown in FIG. 2. The pouch is used until the filter assembly 28 associated with the unobstructed middle passage is no longer effective. At this point, cover 32 is removed from the remaining passage and placed over the middle passage such that the filter in the remaining passage can be utilized.

While only space considerations limit the number of separate passages and separate filter assemblies, it has been found that three filter assemblies will provide sufficient deodorizing capacity for the average useful life of pouch. However, it is to be appreciated that the number of individual passages and filter assemblies employed is not a limitation on the present invention.

While the member 22 of the present invention is illustrated as having a plurality of box-like filter assembly receptacles with essentially planar exterior surfaces, when member 22 is a molded plastic housing it is possible to fashion same with receptacles having exterior surfaces which define a recess into which a correspondingly shaped cap member can be used in a snap-fit fashion to obstruct the passage in a manner which is equivalent to the adhesive coated covers 32.

It should now be appreciated that the present invention relates to a system of multiple deodorizing filters which provide a practical means of extending the useful life of ostomy, wound care and other medical type pouches. Odors are absorbed by an activated carbon filter media held in place on the pouch by a member in the form of an overfilm or molded plastic housing welded to the pouch surface. The member is divided into a plurality passages, each isolated from the others. The filter media has a microporous surface on the inside of the pouch which will allow the passage of gas but is a barrier to liquids. Outlet openings associated with the passages in the member are obstructed with pressure sensitive covers. As one filter loses its odor removal effectiveness, the cover is removed from the next filter and placed over the used filter. The covers are moved to expose each filter in turn.

While only a limited number of preferred embodiments have been disclosed for purposes of illustration, it is obvious that many modifications and variations could be made thereof. It is intended to cover all of these variations and modifications which fall within the scope of the present invention as defined by the following claims.

I claim:

1. A medical device comprising a collection receptacle in the form of a thin walled pouch, a member affixed to the pouch wall comprising a plurality of isolated gas passages, each constituting a vent, separate deodorizing filter means in each one of said passages and means for obstructing the flow through all but a selected one of said passages.

2. The device of claim 1 wherein said passages comprise filter means receiving recesses and said member further comprises gas impervious barriers interposed between said recesses.

3. The device of claim 1 wherein said obstructing means comprises a cover and means for affixing said cover on said member.

4. The device of claim 3 wherein said affixing means is an adhesive coating.

5. The device of claim 1 wherein said member comprises a molded plastic housing.

6. The device of claim 1 wherein said member comprises a stamped overfilm.

7. The device of claim 1 wherein said filter means comprises an activated charcoal filter.

8. The device of claim 1 wherein each of said passages comprise an inlet and an outlet, and when said filter means is interposed between said inlet and said outlet.

9. The device of claim 8 wherein said inlet and said outlet for each of said passages are substantially aligned and wherein gas flows through said filter means between said inlet and said outlet in a direction substantially perpendicular to the surface thereof.

10. The device of claim 1 wherein said filter means is substantially liquid impervious.

11. A medical device comprising a collection receptacle in the form of a thin walled pouch, a member affixed to the pouch wall comprising a plurality of separate passages each one having an inlet and an outlet so as to constitute a vent, separate substantially liquid impervious gas permeable deodorizing filter means interposed between the inlet and outlet within each passage and removable cover means affixable to said member for obstructing the outlets associated with all but a selected one of said passages.

12. The device of claim 11 wherein said inlet and said outlet for each of said passages are substantially aligned and wherein gas flows through said filter means between said inlet and said outlet in a direction substantially perpendicular to the surface thereof.

* * * * *